(12) United States Patent
Skold et al.

(10) Patent No.: US 6,432,907 B1
(45) Date of Patent: Aug. 13, 2002

(54) CATIONIC SUGAR SURFACTANTS FROM ETHOXYLATED AMMONIUM COMPOUNDS AND REDUCING SACCHARIDES

(75) Inventors: Rolf Skold, Stenungsund; Bodil Gustavsson, Angered, both of (SE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/512,856

(22) Filed: Feb. 25, 2000

Related U.S. Application Data

(63) Continuation of application No. PCT/SE98/01433, filed on Aug. 3, 1998.

(30) Foreign Application Priority Data

Aug. 27, 1997 (SE) .............................................. 9703089

(51) Int. Cl.$^7$ ................................................. C11D 3/22
(52) U.S. Cl. ..................... 510/470; 510/238; 510/245; 510/259; 510/362; 510/365; 510/421; 510/504
(58) Field of Search ................................ 510/238, 245, 510/259, 362, 365, 421, 470, 504

(56) References Cited

U.S. PATENT DOCUMENTS

| | | | |
|---|---|---|---|
| 3,931,148 A | 1/1976 | Langdon | 260/210 R |
| 4,968,785 A | * 11/1990 | Moser et al. | 538/4.1 |
| 5,773,595 A | * 6/1998 | Weuthen et al. | 536/17.9 |

FOREIGN PATENT DOCUMENTS

| | | | | |
|---|---|---|---|---|
| DE | 4238211 | * | 1/1994 | |
| DE | 42 38 212 A1 | | 5/1994 | C07H/5/06 |
| EP | 0 432 646 A3 | | 6/1991 | C07H/15/08 |
| EP | 432646 | * | 6/1991 | |
| JP | 4-193891 | | 7/1992 | C07H/15/08 |
| WO | WO 90/15809 | | 12/1990 | C07H/1/00 |

OTHER PUBLICATIONS

International Search Report, dated Nov. 30, 1998.

* cited by examiner

*Primary Examiner*—Charles Boyer
(74) *Attorney, Agent, or Firm*—Ralph J. Mancini

(57) ABSTRACT

The present invention relates to cationic sugar surfactants with improved biodegradability that can be used as hydrotropes for surfactants, especially for nonionic alkylene oxide adducts in alkaline solutions, and as cleaners for hard surfaces. The cationic sugar surfactants contain at least one hydrocarbon group with 6–24 carbon atoms and at least one quaternary ammonium group where at least one substituent is an alkyleneoxy containing group which is connected to a saccharide residue by a glycosidic bond. They are obtained from ethoxylated quaternary ammounium compounds and reducing saccharides or alkyl glycosides.

6 Claims, No Drawings

CATIONIC SUGAR SURFACTANTS FROM ETHOXYLATED AMMONIUM COMPOUNDS AND REDUCING SACCHARIDES

The present application is a continuation of International Patent Application No. PCT/SE98/01433, filed on Aug. 3, 1998, which claims priority of Sweden Patent Application No. 9703089-4, filed on Aug. 27, 1997.

FIELD OF THE INVENTION

The present invention relates to cationic sugar surfactants with improved biodegradability that can be used as hydrotropes for surfactants, especially for nonionic alkylene oxide adducts in alkaline solutions, and as cleaners for hard surfaces. They are obtained from ethoxylated quaternary ammounium compounds and reducing saccharides or alkyl glycosides.

BACKGROUND OF THE INVENTION

Surface active nonionic alkylene oxide adducts are widely used as essential degreasing and/or dispersing components in alkaline cleaning compositions. Their solubility in cleaning composition concentrates is, however, limited in the presence of high amounts of electrolytes, such as alkali and/or alkaline complexing agents.

It is prior known that cationic surfactants, such as ethoxylated fatty amines (about 14–20 moles ethylene oxide per mol fatty amine) that have been quaternized by an alkylating agent, e.g. methyl chloride or dimethyl sulfate, are excellent hydrotropes for nonionic alkylene oxide adducts and are also good cleaners themselves. However, from an environmental point of view they are less desirable, since they are not readily biodegradable.

The main purpose of the present invention is to provide products that are excellent hydrotropes for surfactants.

Another purpose is to provide hydrotropes with improved biodegradability over the prior used cationic surfactants.

Still another purpose is to provide hydrotropes which contribute to the cleaning performance of the surfactants.

It has now been found that said main purpose is achieved by using, as a hydrotrope a cationic sugar surfactant containing at least one hydrocarbon group with 6–24 carbon atoms and at least one quaternary ammonium group where at least one substituent is an alkyleneoxy containing group which is connected to a saccharide residue by a glycosidic bond.

SUMMARY OF THE INVENTION

The present invention generally relates to a cationic sugar surfactant containing at least one hydrocarbon group with 6–24 carbon atoms and at least one quaternary ammonium group where at least one substituent is an alkyleneoxy containing group which is connected to a saccharide residue by a glycosidic bond, and more particularly, the use of said sugar surfactant as a hydrotrope for surfactants.

DETAILED DESCRIPTION OF THE INVENTION

In accordance with the present invention, new hydrotropes which contribute to the cleaning performance of the surfactants have been found. These hydrotropes comprise a cationic sugar surfactant containing at least one hydrocarbon group with 6–24 carbon atoms and at least one quaternary ammonium group where at least one substituent is an alkyleneoxy containing group which is connected to a saccharide residue by a glycosidic bond.

Preferably the substituent has the formula $(AO)_s(G)_g$ where AO is an alkyleneoxy group with 2–4 carbon atoms, G is a saccharide residue, g is a number from 1 to 10 and s is a number from 1 to 12.

The cationic sugar surfactant according to the invention may be produced by reacting
   a) an amine compound containing at least one hydrocarbon group with 6–24 carbon atoms and at least one quaternary ammonium group, where at least one substituent is a hydroxyalkyl containing group, and
   b) a reducing saccharide or an alkyl glycoside where the alkyl group has 1–8 carbon atoms, at least partially in the presence of an acid. The substituent attached to the quaternary ammonium group has preferably the formula $(AO)_s(G)_g$, where AO is an alkyleneoxy group with 2–4 carbon atoms, G is a saccharide residue, g is a number from 1 to 10 and s is a number from 1 to 12.

Suitable sugar surfactants according to the invention have the formula

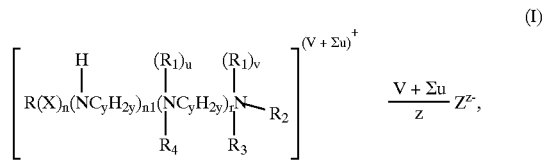

(I)

where R is an aliphatic group with 6–24, preferably 8–20 carbon atoms; $R_1$ is an aliphatic group with 1–4 carbon atoms or $(AO)_s(G)_p$; $R_2$, $R_3$ and $R_4$ are a group $(AO)_s(G)_p$, an aliphatic group with 1–24 carbon atoms or a hydroxyalkyl group with 2–4 carbon atoms; AO is an alkyleneoxy group with 2–4 carbon atoms; s is 0–12, preferably 1–6 and $\Sigma s=1–25$, preferably 3–15; G is a saccharide residue which is connected to the rest of the molecule by a glycosidic bond and p (the degree of polymerisation) is 0–10 and $\Sigma p=1–20$; r=0–3; y=2–3; X=CO or $COO(AO)_t(C_qH_{2q})$ or $O(AO)_t(C_qH_{2q})$; n=0 or 1; $n_1$ is 0 except when X is CO, then $n_1$ is 1; q=2–4; t=0–2; u=0 or 1 and v=0 or 1, provided that the sum (v+$\Sigma$ u) is 1–3, preferably 1; Z is an anion, preferably a monovalent anion, such as Cl⁻ or methyl sulphate and z is the charge of the anion Z. The nitrogen atoms where u or v is 1 are quaternary and thus have a permanent positive charge. These cationic sugar surfactants have, in comparison with the prior known cationic hydrotropes, an essentially improved biodegradability. They are also comparable or better hydrotropes for surfactants, especially nonionic alkoxylates, and combine the improved biodegradability and good hydrotropy with a surprisingly large contribution to the cleaning performance of cleaning compositions as well as a valuable dispersing effect.

The product (I) can be produced by reacting a) a reducing saccharide or an alkyl glycoside and b) a quaternary ammonium compound having the formula

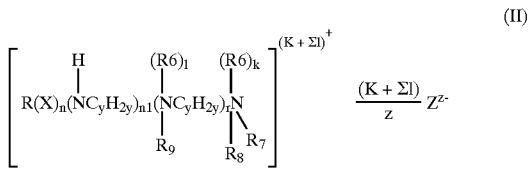

(II)

where $R_6$ is independently an aliphatic group with 1–4 carbon atoms or —$CH_2CH_2OH$; $R_7$, $R_8$ and $R_9$ independently are a group (AO)$_s$, an aliphatic group with 1–24 carbon atoms or a hydroxyalkyl group with 2–4 carbon atoms; l=0 or 1 and k=0 or 1, provided that the sum (k+Σ l) is 1–3, preferably 1; and R, AO, s, X, n, n$_1$, y and r have the same meaning as in formula I. The nitrogen atoms where k or l is 1 are quaternary and thus have a permanent positive charge. Since compounds II are rather hydrophobic due to a limited number of oxyethylene units, they exhibit no or only limited hydrotropic effects. Also the cleaning ability of compounds having the formula II is poor. The obtained reaction mixture contains essential amounts of both the cationic sugar surfactant I and the quaternary ammonium compound II. This product mixture can advantageously be used without any purification as a hydrotrope. Normally the ratio between the cationic sugar surfactant I and the quaternary ammonium compound II is from 1:3 to 9:1.

Suitable examples of the cationic sugar surfactants and the quaternary ammonium compounds are those having the formulae

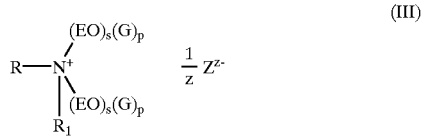

(III)

where R is an aliphatic group with 6–24, preferably 8–20 carbon atoms; R$_1$ is an aliphatic group with 1–4 carbon atoms or the group C$_2$H$_4$O(G)$_p$; G is a saccharide residue that is connected to the polyethyleneoxy chain by a glycosidic bond and p (the degree of polymerisation) is 0–10, preferably 0–5, Σ p being 1–15, preferably 1–8; EO is an ethyleneoxy group; s is 0–12; Σ s is 2–15, preferably 5–12; Z and z have the meaning mentioned in formula I and

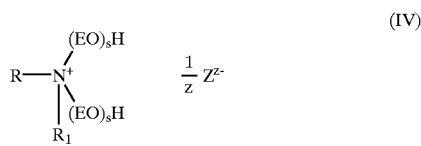

(IV)

where R, R$_1$, EO, z, Z and s have the same meaning as in formula III except that p in the group R$_1$ is 0, respectively.

Suitable examples of hydrophobic groups R in formula 1–IV are: hexyl, 2-ethylhexyl, octyl, decyl, cocoalkyl, lauryl, oleyl, rape seed alkyl and tallow alkyl.

The cationic sugar surfactants III are easily produced by reacting a reducing saccharide and the quaternary ammonium compound of formula IV. The reaction mixtures containing essential amounts of both compound III and IV are preferably used as hydrotropes without any separation of the compounds, mainly because such a separation is a costly operation. The relation between cationic sugar surfactant and the quaternary ammonium compound could vary between 1:3 and 9:1, preferably between 2:3 and 9:1.

Cationic surfactants containing sugar residues are known by the publications DE 4 413 686 and JP 4-193891. In DE 4 413 686 surfactants containing quaternary ammonium groups are prepared by reacting glycosides with quaternary halogenated compounds or quaternary epoxy compounds. The linkage between the sugar residue and the cationic part is an ether linkage. The products could also be prepared by first reacting the glycoside with a halogenated compound followed by reacting with an amine. The applications for these products are for example as components in detergent mixtures.

In JP 4-193891 cationic sugar surfactants are prepared by the following procedure: A reducing saccharide or an alkyl glycoside is reacted with a polyalkyleneglycol halohydrin in the presence of an acid catalyst to obtain a polyoxyalkylene halohydrin glycoside. This product is further reacted with an amine compound, whereby the chlorine is displaced, and the resulting amine is then quaternized by e.g. methyl chloride or dimethyl sulphate. The quaternization could also take place by directly reacting the halogenated intermediate with a tertiary amine.

These products are used as mild surfactants with good biodegradability. However, the procedure of making them requires the production of the intermediate polyalkyleneglycol monohalohydrin where the starting material is 2-chloroethanol, which nowadays is only produced on a small scale and further is a highly toxic and irritant substance. To obtain the polyalkyleneglycol monochlorohydrine, the 2-chloroethanol is alkoxylated in the presence of an acid catalyst. The glycosidation process which then follows, makes use of a laborious and costly work-up procedure with distillation or solvent extraction, which is performed in order to get rid of the unreacted polyalkyleneglycol halohydrin.

The process involves at least the following steps; preparation of the polyalkyleneglycol halohydrin, preparation of polyoxyalkylene halohydrin glycoside and at last preparation of the quaternary ammonium alkylaminopolyoxyalkylene glycoside by reaction with a tertiary amine. If a primary or secondary amine is used instead, additional steps are required to obtain a quaternarization. Furthermore, in the last mentioned case inorganic salt is produced, which is removed by filtering the product.

The present invention utilizes a different synthetic route to obtain cationic sugar surfactants. The general procedure for making products with the formula I according to this invention involves the one-step reaction between a quaternary alkoxylated ammonium compound II and a reducing saccharide or an alkyl glycoside. The compound II is obtained by standard procedures known to those skilled in the art. The reaction between II and the saccharide is a glycosidation and can be performed as follows: Compound II is heated to a reaction temperature of from 85 to 120° C. and the saccharide is added in an amount of between 0.5 and 12, preferably between 1.5 and 6 mole saccharide/mole quaternary ammonium compound. Depending on the amine used, the cationic sugar surfactant I can contain one, two, three or more saccharide residues (G)$_p$, where G and p have the meaning mentioned in formula I. The saccharide reactant is preferably added in excess with regard to the number of glycoside bonds desired, since the saccharide also has a tendency to condensate with more saccharide units. This condensation is indicated in the formulae by the polymerisation degree p. The reaction is catalyzed by strong acid, e.g. p-toluenesulphonic acid or sulphuric acid, which may be added to the reaction mixture in an amount of between 0.1 and 4, preferably between 0.7 and 2.1 mole % of compound II. If the compound II is reacted with an alkyl glycoside, the process is a trans-glycosidation reaction. To aid the removal of water or alcohol from the reaction mixture, the process is carried out under reduced pressure (50–70 mbar). The reaction time is very dependent on the temperature and varies between less than one hour to six hours. When no more water or alcohol distills off the product is neutralized.

The method for producing the cationic sugar surfactant of this invention is quick and convenient. The starting materials are readily available and the process does not require any work-up of the reaction mixture. There is no need to add an excess of the quaternary ammonium compound in the glycosidation reaction. Rather the saccharide or alkyl glycoside is added in excess to give products with several saccharide units attached.

In aqueous alkaline solution the cationic sugar surfactants according to the present invention exhibit excellent hydrotropic effects for surfactants like nonionic alkoxylates. These alkoxylates could contain a hydrophobic group of 8–50 carbon atoms, which preferably is a hydrocarbon group or an acyl group containing from 8 to 24 carbon atoms. Suitable examples of such nonionic surfactants are alkylene oxide adducts obtained by alkoxylation of an alcohol, an amine or an amide. One example is compounds having the formula $$R'O(AO)_aH \tag{V}$$

wherein R' is a hydrocarbon group having 8–18 carbon atoms, a is from 2–12, preferably 3–10, and AO is an alkyleneoxy group having 2–4 carbon atoms, the number of ethyleneoxy groups being at least 50% of the total number of alkyleneoxy groups. The R' group may be branched or straight, saturated or unsaturated, aromatic or aliphatic. Examples of hydrocarbon groups R' are: 2-ethylhexyl, octyl, decyl, cocoalkyl, lauryl, oleyl, rape seed alkyl, tallow alkyl, octylphenol and nonylphenol. Especially suitable hydrocarbon groups are those obtained from oxoalcohols, Guerbet alcohols, methyl substituted alcohols with 2–4 groups having the formula —CH(CH$_3$)— included in the alkyl chain, and straight alcohols.

Another example of suitable nonionic surfactants are compounds having the formula

(VI)

wherein R" is a hydrocarbon group or an acyl group having 8–18 carbon atoms, AO has the same meaning as in formula V and the sum of b1 and b2 is 2–12, preferably 3–10. The hydrocarbon group and the acyl group can be aromatic or aliphatic, branched or straight, saturated or unsaturated. Examples of suitable groups are 2-ethylhexyl, octyl, decyl, cocoalkyl, lauryl, oleyl, rape seed alkyl, tallow alkyl and the corresponding aliphatic acyl groups. If R" in the formula VI is an acyl group, preferably one of b1 and b2 is 0, whereas if the nitrogen atom is an amine nitrogen, b1 and b2 are both preferably different from zero.

The cationic sugar surfactants of the invention are normally used in alkaline compositions having a pH-value above 8, preferably from 9–13, for use in the cleaning of hard surfaces, like degreasing of metal and plastic, dish washing and car washing. A suitable formulated composition concentrate may contain a) 0.5–20% by weight of a surface active nonionic alkylene oxide adduct,
b) 0.2–20% by weight of a mixture consisting of a cationic sugar surfactant according to formula I, and a compound of formula II present in a weight ratio of from 1:3 to 9:1,
c) 0.5–30% by weight of alkali and/or polyelectrolytes like alkaline complexing agents,
d) 0–10% by weight of other conventional components in cleaning compositions, like other surfactants, other hydrotropes, thickening agents, solvents, colorants, soil antiredeposition agents, defrosting stabilizers, preservatives, corrosion inhibitors, foam regulators, etc., and
e) 30–98.8% by weight of water.

The concentrates are normally diluted with water prior to use, and the ready-to-use solution may be diluted to a concentration of from 0.05% to 15% by weight of alkali and/or alkaline complexing agents.

The complexing agent in the concentrate can be inorganic as well as organic. Typical examples of inorganic complexing agents used in the alkaline cleaning concentrate are alkali salts of silicates and phosphates, such as sodium tripolyphosphate, sodium orthophosphate, sodium pyrophosphate, sodium phosphate, polymer sodium phosphates and the corresponding potassium salts. Typical examples of organic complexing agents are alkaline aminopolyphosphonates, organic phosphates, polycarboxylates, such as citrates; amino-carboxylates, such as sodium nitrilotriacetate (Na$_3$NTA), sodium ethylenediaminetetraacetate, sodium diethylenetriaminepentaacetate, sodium 1,3-propylenediaminetetraacetate and sodium hydroxyethylethylenediaminetriacetate.

The following examples are illustrative of the invention and are not to be construed as limiting thereof.

In Examples 1–5 the production of some representatives of the quaternary sugar surfactants of the present invention is described. In Example 6 the improved biodegradability of the quaternary sugar surfactants as compared to prior art hydrotropes is demonstrated. In Examples 7 and 8, it is shown that the cationic surfactants of the present invention are better hydrotropes than the cationic hydrotropic compounds of the prior art both with respect to the amount of hydrotrope needed to obtain a clear solution with given concentrations of nonionic surfactant and alkaline complexing agents, and with respect to the amount of complexing agent possible to include in an isotropic alkaline cleaning concentrate. In Example 9 the improved cleaning ability as compared to prior art hydrotropes is demonstrated.

EXAMPLE 1

1 mole of a cocoamine ethoxylate (1 mole cocoamine+8 mole ethylene oxide) quaternized with methyl chloride was heated to 100° C. Two moles of glucose and 1.4 mole % (referring to the quaternary compound) of p-toluenesulphonic acid was added to the quaternary ammonium compound. The reaction mixture was kept between 98 and 106° C. under reduced pressure (50–70 mbar) for 2.5 hours. Finally the product was neutralised by first adding sodium methylate and then sodium carbonate. The product mixture contained about 42% (w/w) unglucosidised starting material and 2.0% free glucose according to GC. The structure of a glucosidised product according to formula III, where R=cocoalkyl, R$_1$=methyl, $\Sigma$ s=8, $\Sigma$ p=2 and Z=Cl was confirmed by $^1$H and $^{13}$C-NMR.

EXAMPLE 2

The same procedure as described in Example 1 was followed, but with the exception that 3 moles of glucose was added, the temperature was between 95 to 99° C. and the reaction time was 3.3 hours. The product mixture contained about 34% (w/w) unglucosidised material and 1% free glucose. A glucosidised product according to formula III, where R=cocoalkyl, R$_1$=methyl, $\Sigma$ s=8, $\Sigma$ p=3 and Z=Cl was obtained.

EXAMPLE 3

1 mole of an oleylamine ethoxylate (1 mole oleylamine+ 12 mole ethylene oxide) quaternised with methyl chloride, was reacted with 3 moles of glucose by the procedure described in Example 1, with the exception that the reaction temperature was between 98 to 100° C. and the reaction time was 3.75 hours. The product mixture contained about 55% (w/w) unglucosidised starting material and 1.7% free glucose. A glucosidised product according to formula III, where R=oleyl, $R_1$=methyl, $\Sigma$ s=12, $\Sigma$ p=3 and Z=Cl was obtained.

EXAMPLE 4

1 mole of an oleylamine ethoxylate (1 mole oleylamine+ 11 mole ethylene oxide), quaternised with methyl chloride, was reacted with 3 moles of glucose by the procedure described in Example 1, with the exception that the reaction temperature was 96° C. and the reaction time was 4 hours. The product mixture contained about 63% (w/w) unglucosidised starting material and 8.7% free glucose. A glucosidised product according to formula III, where R=oleyl, $R_1$=methyl, $\Sigma$ s=11, $\Sigma$ p=3 and Z=Cl was obtained.

EXAMPLE 5

1 mole of a cocoamine ethoxylate (1 mole cocoamine+8 mole ethylene oxide), quaternised with ethylene oxide, was reacted with 4 moles of glucose by the procedure described in Example 1, with the exception that the reaction temperature was between 90 to 97° C. and the reaction time was 3.5 hours. The product mixture contained about 39% (w/w) unglucosidised starting material and 4% free glucose. A glucosidised product according to formula III, where R=cocoalkyl, $R_1$=$C_2H_4O(G)_p$, $\Sigma$ s=8, $\Sigma$ p=4 and Z=Cl was obtained.

EXAMPLE 6

Biodegradability tests were performed with the "closed bottle test" as described in OECD Test 301D. Cocoamine with 15 oxyethylene units, that has been quaternised by dimethyl sulphate, which is an example of prior art hydrotrope, was used as a reference. This compound reached 17% biodegradation after 28 days. The product obtained in Example 1 exhibited 41% biodegradation at the same occasion with the same test method. Accordingly, the biodegradation was more than doubled with the product in Example 1 as compared to the prior art cationic hydrotrope that was used as a reference.

TABLE 1

| Product Example nr | % biodegradation |
| --- | --- |
| 1 | 41 |
| 2 | 31 |
| 3 | — |
| 4 | 35 |
| 5 | — |
| Reference | 17 |

— = not determined

EXAMPLE 7

To evaluate the efficiency as a hydrotrope of the cationic sugar surfactants of this invention the following formulation was used:

| Ingredient | % by weight |
| --- | --- |
| Nonionic surfactant | 5 |
| Sodium metasilicate × $5H_2O$ | 4 |
| Tetrapotassium pyrophosphate | 6 |
| Reaction product containing hydrotrope | X |
| Water | [100 − (15 + X)] |

The nonionic surfactant used was a $C_{9-11}$ alcohol with a linearity above 80% w/w that had been ethoxylated with 4 moles of ethylene oxide per mole alcohol in the presence of a narrow range catalyst. X is the amount of reaction product containing hydrotrope from Example 1–5 needed to obtain a clear solution between 10 and 40° C. The reference used is the same as the reference for the biodegradability tests. The results from this investigation of hydrotropic efficiency are collected in Table 2.

TABLE 2

| Formulation no | Hydrotrope | % by weight of hydrotrope mixture | % active amount of glucosidised hydrotrope used |
| --- | --- | --- | --- |
| I | Example 1 | 3 | 1.7 |
| II | Example 2 | 2.9 | 1.9 |
| III | Example 3 | 3.3 | 1.4 |
| IV | Example 4 | 3.0 | 0.8 |
| V | Example 5 | 4.9 | 2.8 |
| A | Reference | 3.0 | 3.0 |

EXAMPLE 8

To solutions containing 5% nonionic surfactant and different amounts of $Na_3NTA$ kept at 40° C. the hydrotropes were added in the smallest amounts possible to make the turbid solutions clear. To determine the clearness interval the mixtures were then heated up to the point when they went turbid again and thereafter chilled to 0° C. The nonionic surfactant and the reference used are the same as in Example 7. The results from the investigation are collected in Table 3.

TABLE 3

| Hydrotrope, Example No | % by weight of mixture containing hydrotrope | % by weight $Na_3NTA$ | Clearness interval, ° C. |
| --- | --- | --- | --- |
| 4 | 3.5 | 10 | 0–79 |
| 4 | 4.5 | 15 | 0–60 |
| 4 | 6 | 20 | 0–55 |
| 4 | 10 | 25 | 0–48 |
| Reference | 2.5 | 10 | 0–45 |
| Reference | 4 | 15 | 0–43 |

EXAMPLE 9

To evaluate the cleaning efficiency of the formulations in example 7 containing the cationic sugar surfactants the following cleaning test was used: White painted plates were smeared with an oil-soot mixture obtained from diesel engines. 25 ml of the test solutions, in this case the formulations in Example 7 diluted 1:40, are poured onto the top of the oil-smeared plates and left there for one minute. The plates are then rinsed off with a rich flow of water. All solutions and the water are kept at a temperature of about 15–20° C. All reference solutions are placed on the same plate as the test solutions. The cleaning ability is measured with a Minolta Chroma Meter CR-200 reflectometer using the lightness values, and the result is presented as the remaining % loss of lightness. Accordingly, the lower the values are, the better the cleaning ability. The results are collected in Table 4.

TABLE 4

| Formulation nr | Active content of hydrotrope in formulation | % loss of lightness at 1:40 dilution |
|---|---|---|
| I | 1.7 | 4.6 |
| II | 1.9 | 6.1 |
| III | 1.4 | 5.3 |
| IV | 0.8 | 3.6 |
| V | 2.8 | 5.0 |
| A | 3.0 | 14.4 |

As can bee seen from Table 4, the cationic sugar surfactants are more efficient cleaners than the prior art hydrotropes.

We claim:

1. A method of increasing the solubility of a surfactant composition which comprises at least one surface active nonionic alkylene oxide adduct, wherein said method comprises adding a hydrotrope to said composition, said hydrotrope comprising a cationic sugar surfactant containing at least one hydrocarbon group with 6–24 carbon atoms and at least one quaternary ammonium group where at least one substituent is an alkyleneoxy containing group which is connected to a saccharide residue by a glycosidic bond.

2. The method of claim 1 wherein in said cationic sugar surfactant, the substituent has the formula $(AO)_s(G)_g$, where AO is an alkyleneoxy group with 2–4 carbon atoms, G is a saccharide residue, g is a number from 1 to 10 and s is a number from 1–12.

3. The method of claim 1 wherein said cationic sugar surfactant has the formula

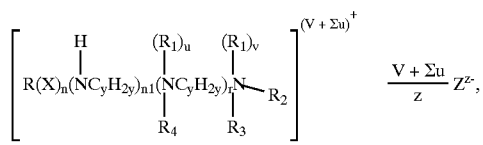

where R is an aliphatic group with 6–24 carbon atoms; $R_1$ is an aliphatic group with 1–4 carbon atoms or $(AO)_s(G)_p$; $R_2$, $R_3$ and $R_4$ independently are a group $(AO)_s(G)_p$, an aliphatic group with 1–24 carbon atoms or a hydroxyalkyl group with 2–4 carbon atoms with the proviso that at least one of R1, R2, R3, and R4 is the group $(AO)_S(G)_P$; AO is an alkyleneoxy group with 2–4 carbon atoms; s is 0–12 and Σ s=1–25; G is a saccharide residue which is connected to the rest of the molecule by a glycosidic bond and p (the degree of polymerisation) is 0–10; Σ p=1–20; r =0–3; y=2–3; X=CO or $COO(AO)_t(C_qH_{2q})$ or $O(AO)_t(C_qH_{2q})$; n=0 or 1;

$n_1$ is 0 except when X is CO, then $n_1$ is 1; q=2–4; t=0–2; u=0 or 1 and v=0 or 1, provided that the sum (v+Σ u) is 1–3; Z is an anion and z is the charge of the anion Z.

4. The method of claim 3, where the cationic sugar surfactant is present in a mixture with a quaternary ammonium compound having the formula

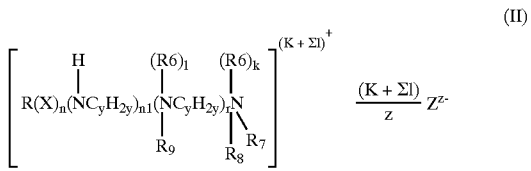

where $R_6$ is independently an aliphatic group with 1–4 carbon atoms or —$CH_2CH_2OH$; $R_7$, $R_8$, and $R_9$ independently are a group $(AO)_s$, an aliphatic group with 1–24 carbon atoms or a hydroxyalkyl group with 2–4 carbon atoms; I=0 or 1 and k=0 or 1, provided that the sum (k+Σ I) is 1–3; and R is an aliphatic group with 6–24 carbon atoms, AO is an alkyleneoxy group with 2–4 carbon atoms, s is 0–12 and Σ s=1–25, X=CO or $COO(AO)_t(C_qH_{2q})$ or $O(AO)_t(C_qH_{2q})$; n=0 or 1; $n_1$ is 0 except when X is CO, then $n_1$ is 1; q=2–4; t=0–2; r=0–3; y=2–3, in a weight ratio 1:3–9:1.

5. The method of claim 3 wherein the cationic sugar surfactant has the formula

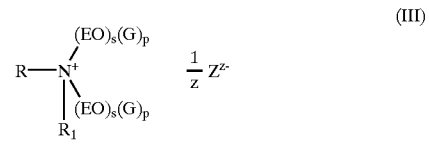

where R is an aliphatic group with 6–24 carbon atoms; $R_1$ is an aliphatic group with 1–4 carbon atoms or the group $C_2H_4O$ $(G)_p$; G is a saccharide residue that is connected to the poly-ethyleneoxy chain by a glycosidic bond and p (the degree of polymerisation) is 0–10; Σ p is 1–15; EO is an ethyleneoxy group; s is 0–12; Σ s is 2–15; Z is an anion and z is the charge of the anion Z.

6. The method of claim 5, wherein the cationic sugar surfactant is present in a mixture with a quaternary ammonium compound having the formula

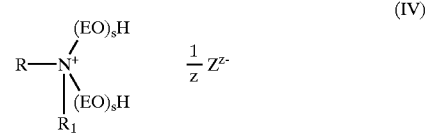

where R is an aliphatic group with 6–24 carbon atoms; $R_1$ is an aliphatic group with 14 carbon atoms or the group $C_2H_4OH$; EO is an ethyleneoxy group; s is 0–12; Σ is 2–15; Z is an anion and z is the charge of the anion Z, in a weight ratio 1:3–9:1.

* * * * *

UNITED STATES PATENT AND TRADEMARK OFFICE
CERTIFICATE OF CORRECTION

PATENT NO.      : 6,432,907 B1                                                Page 1 of 1
DATED           : August 13, 2002
INVENTOR(S)     : Skold et al.

It is certified that error appears in the above-identified patent and that said Letters Patent is hereby corrected as shown below:

Column 10,
Line 56, "14 carbon" should read -- 1-4 carbon --

Signed and Sealed this

Sixth Day of May, 2003

JAMES E. ROGAN
*Director of the United States Patent and Trademark Office*